(12) United States Patent
Xu

(10) Patent No.: US 9,573,932 B2
(45) Date of Patent: Feb. 21, 2017

(54) SYNTHESIS OF INTERMEDIATES IN THE PREPARATION OF ALK INHIBITOR

(71) Applicant: Yong Xu, San Diego, CA (US)

(72) Inventor: Yong Xu, San Diego, CA (US)

(*) Notice: Subject to any disclaimer, the term of this patent is extended or adjusted under 35 U.S.C. 154(b) by 0 days.

(21) Appl. No.: 14/635,066

(22) Filed: Mar. 2, 2015

(65) Prior Publication Data

US 2016/0257667 A1   Sep. 8, 2016

(51) Int. Cl.
*C07D 401/10* (2006.01)
*C07D 413/04* (2006.01)
*C07D 211/58* (2006.01)
*C07D 209/18* (2006.01)

(52) U.S. Cl.
CPC ........... *C07D 401/10* (2013.01); *C07D 211/58* (2013.01); *C07D 209/18* (2013.01); *C07D 413/04* (2013.01)

(58) Field of Classification Search
CPC .. C07D 515/00; C07D 413/04; C07D 295/037
USPC ........................................................ 544/130
See application file for complete search history.

(56) References Cited

U.S. PATENT DOCUMENTS

2012/0083488 A1* 4/2012 Kinoshita ............ C07D 209/56
514/217.03

OTHER PUBLICATIONS

Cole, P. "Alectinib Hydrochloride: ALK Receptor Tyrosine Kinase Inhibitor Oncolytic" Drugs of the Future (2013), 38 (12), pp. 799-805.*

* cited by examiner

*Primary Examiner* — Alicia L Otton
*Assistant Examiner* — Sagar Patel
(74) *Attorney, Agent, or Firm* — Kile Park Reed & Houtteman PLLC

(57) ABSTRACT

The present disclosure provides a method for preparing a compound of formula XVII, comprising: (1) contacting a compound of formula XIV with a compound of formula 3 to obtain a compound of formula 2; and (2) contacting the compound of formula 2 with a compound of formula 4 to obtain a compound of formula XVII. The method is low toxicity, cheap, easy to get, environmentally and friendly, and is economical and industrially applicable.

13 Claims, No Drawings

SYNTHESIS OF INTERMEDIATES IN THE PREPARATION OF ALK INHIBITOR

FIELD

The present invention relates to a chemical medicine field, it relates generally to the synthesis of intermediates in the preparation of ALK inhibitor. Specifically, the invention relates to the method for the preparation of the intermediates for alectinib.

BACKGROUND

Anaplastic lymphoma kinase (ALK) inhibitors are efficient anti-cancer drugs that act on tumours with variations of anaplastic lymphoma kinase (ALK) such as an EML4-ALK translocation. About 4-7% of non-small cell lung carcinomas (NSCLC) have EML4-ALK translocations.

The second-generation compound alectinib (RG-7853; AF-802; CH5424802; RO5424802) has been found to be a potent and selective ALK inhibitor. Roche and its subsidiary Chugai have developed alectinib (trade name Alecensa). The product is indicated in Japan for the oral treatment of advanced, recurrent or unresectable ALK fusion gene-positive NSCLC. In September 2014, alectinib was launched in Japan for the treatment of ALK-positive NSCLC. In July 2014, a phase III trial for ALK-positive NSCLC began in the US. In October 2014, the company was planning to file marketing applications in the US and Europe post 2017. Initial studies required eight capsules per dose, however a new higher-strength formulation had been developed by May 2014.

CH5424802 is described chemically as 9-ethyl-6,6-dimethyl-8-(4-morpholinopiperidin-1-yl)-11-oxo-6,11-dihydro-5H-benzo[b]carbazole-3-carbonitrile, and has the structural formula shown as Formula 1:

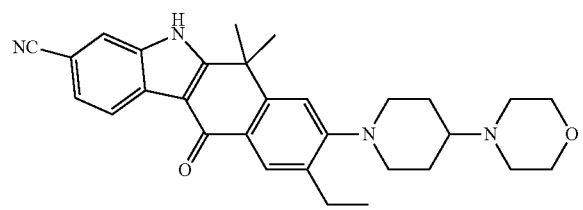

1

Compound XIV, compound 2, compound 3, compound XVII and compound XVIII, the intermediates for preparing CH5424802, have the structural formulas shown as below:

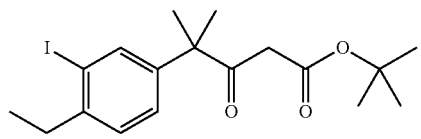

XIV

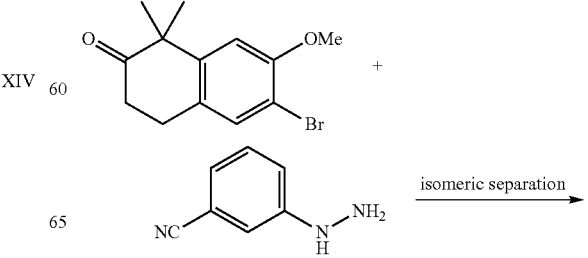

2

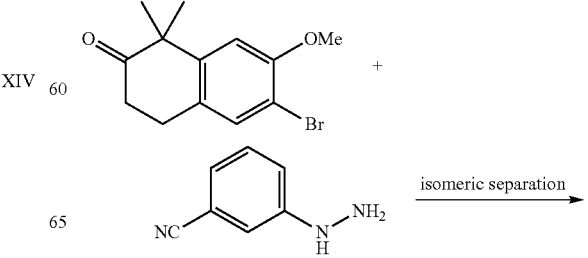

3

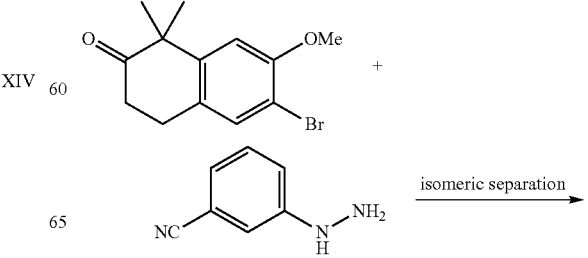

XVII

XVIII

There are two different ways of preparing CH5424802 product (compound 1) and the intermediates thereof, described in Drug of the Future, 2013, 38(12), 799-805, and Bioorganic & Medicinal Chemistry, 2012, 20(3), 1271-1280, and the international patent application Publication No. WO2010/143664, all of which are incorporated by references.

In the prior art of scheme 1, the synthetic route of CH5424802 is shown below.

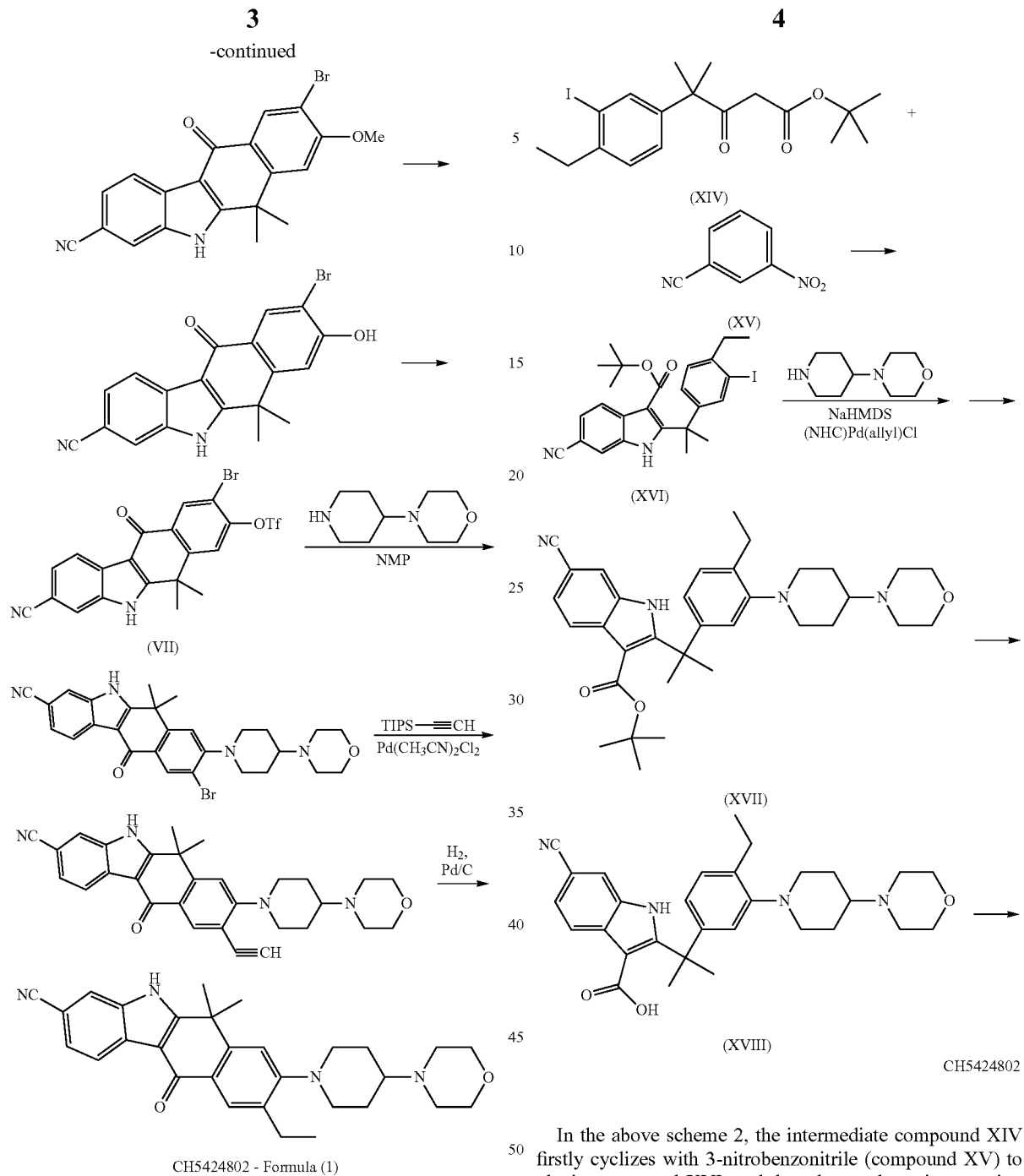

In the above-scheme 1, the intermediate 6-bromo-7-methoxy-1,1-dimethyl-3,4-dihydronaphthalen-2(1H)-one reacts with 3-hydrazinylbenzonitrile to occur cyclization, and further isomeric separation by crystallization proceeds on cyclopentyl methyl ether (CPME) to obtain 9-bromo-8-methoxy-6,6-dimethyl-11-oxo-6,11-dihydro-5H-benzo[b]carbazole-3-carbonitrile, and then compound VII is obtained.

Compound VII is condensated with 4-(piperidin-4-yl)morpholine, and then expensive and harmful heavy metal palladium is used as catalyst to obtain CH5424802.

In the prior art of scheme 2, the synthetic route of CH5424802 is shown below.

In the above scheme 2, the intermediate compound XIV firstly cyclizes with 3-nitrobenzonitrile (compound XV) to obtain compound XVI, and then the condensation reaction of compound XVI with 4-(piperidin-4-yl)morpholine fragment, sodiobis(trimethylsilyl)amine (NaHMDS) and (NHC)Pd(allyl)Cl proceed in strictly anhydrous environment to obtain compound XVII, and subsequently the resultant compound XVII is subjected to deprotection reaction to get compound XVIII. Finally, cyclization occurs to obtain CH5424802.

For schemes 1 and 2, both reactions are carried out before the cyclization with 3-hydrazinylbenzonitrile or 3-nitrobenzonitrile, then followed by the condensation reaction with 4-(piperidin-4-yl)morpholine fragment to obtain CH5424802 finally. The routes are too long and the methods above need isomeric separation, expensive heavy metal palladiun as catalyst which is harmful to the environment. The use of heavy metal in these two reactions results in a greater amount of solid waste having a great influence on the final product of metal residues.

SUMMARY

It is an object of the present disclosure to devise a method for preparing intermediates of ALK inhibitor to improve the process for the synthesis of ALK inhibitor alectinib (CH5424802), thereby avoiding at least one of the disadvantages described above.

It has now been found, surprisingly, a compound of formula XIV is first subjected to a coupling reaction with 4-(piperidin-4-yl)morpholine fragment, and then the resultant product is subjected to a cyclization reaction with 3-nitro-chloro-acrylonitrile. A catalyst containing copper or iron was used as catalyst, which are low toxicity, cheap, easy to get, environmentally and friendly, and the method of present disclosure may avoid the above mentioned disadvantages, and are economical and industrially applicable. It reduce the cost of industrial production greatly and it is a green synthesis route.

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

In this article, the term "base" herein should be understood broadly, means any substances producing more hydroxide ions (OH⁻) than H⁺ in aqueous solutions, non-limiting examples of the base may be basic salt, alkali or alkaline.

According to the present disclosure, it is devised a process of preparing a compound of formula XVII:

XVII

The technical solutions of the present disclosure include: compound 2 is prepared by a process comprising reacting compound XIV with compound 3, compound XVII is prepared by a process comprising reacting compound 2 with compound 4.

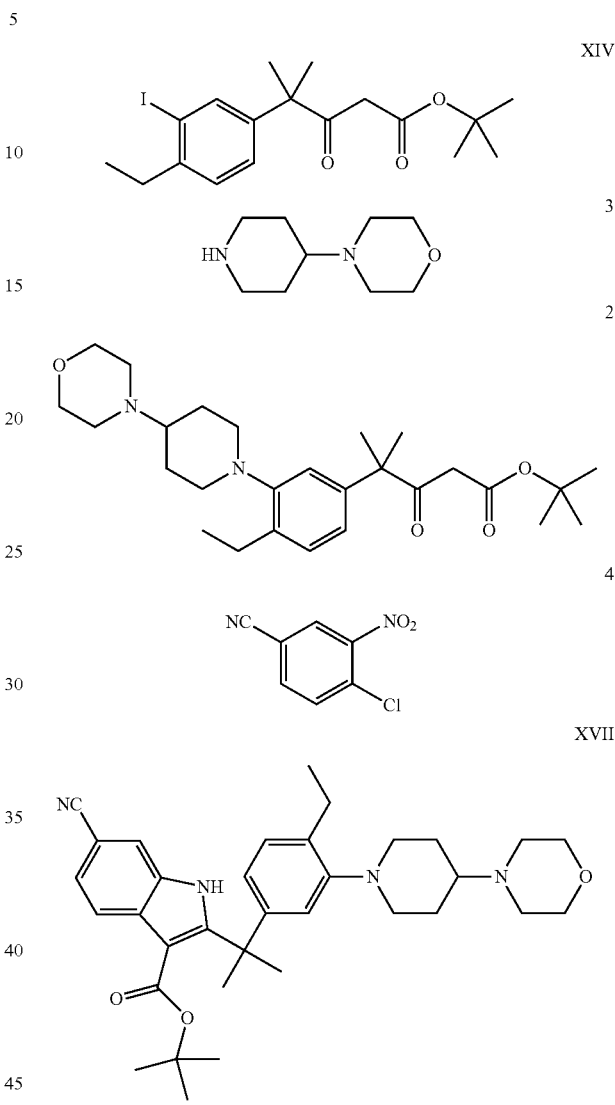

The compound XVII is a key intermediate for preparing alectinib, it may be deprotected (removing the t-Bu protective group) to get compound XVIII, then cyclized to obtain compound 1 (alectinib, CH5424802), thereby improving the process for the synthesis of ALK inhibitor alectinib.

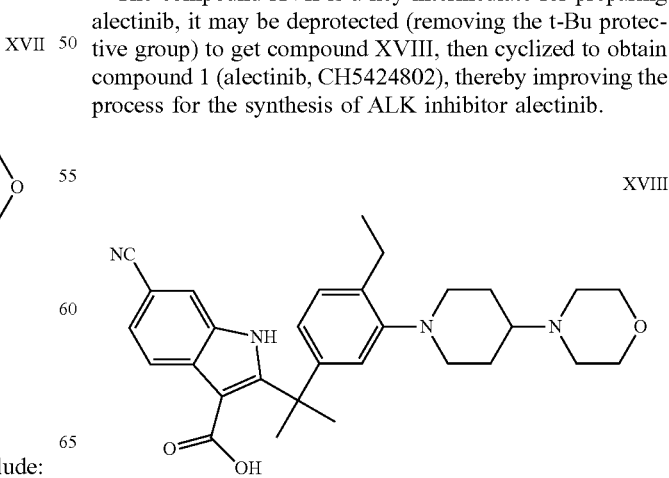

-continued

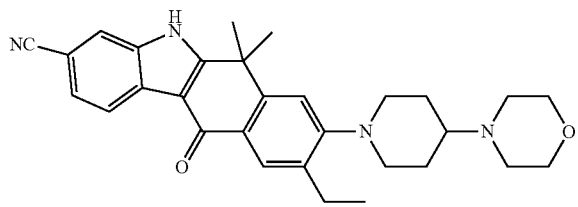

According to an embodiment of the present disclosure, the preparation method of compound XVII (ALK inhibitor CH5424802 (alectinib)) includes the following steps:

Step (A): coupling reaction: compound XIV is contacted with compound 3 to give compound 2.

Step (B): cyclization reaction: compound 2 is contacted with compound 4 to give compound XVII.

Then, compound XVII may be subjected to deprotection reaction to give compound XVIII. And compound XVIII may be subjected to cyclization reaction with acetic anhydride and N,N-diisopropylethylamine (DIEA) to give compound 1.

In some embodiments, in the method disclosed herein, the preparation method of the present invention is as follows.

Step (A): The coupling reaction may be taken place when compound XIV reacts with compound 3 to give compound 2, in the presence of a catalyst containing copper or iron, and a first base.

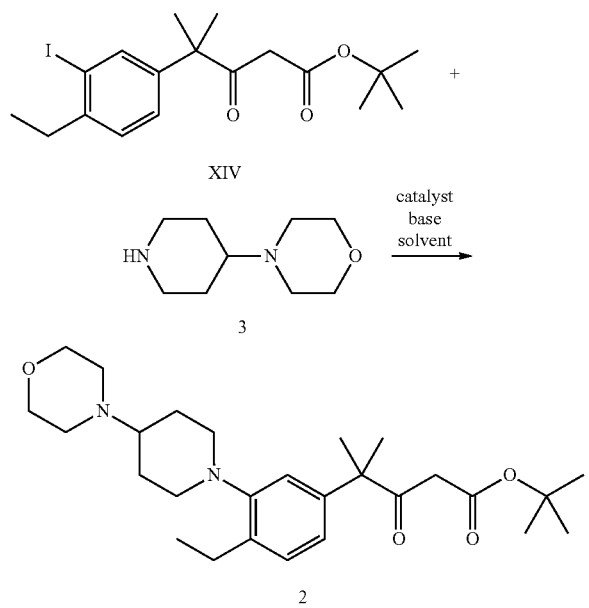

Firstly, in a first reactor, the catalyst and the first base may be dissolved in a first solvent. Subsequently, compound XIV, compound 3 may be added to this mixture. Then the first reactor may be sealed under nitrogen, and the mixture may be heated and kept at 80°~135°, stirred for 10 hours to 32 hours. After cooling to room temperature, the mixture may be diluted with dichloromethane and filtered. The filtrate may be washed twice with water, and the combined aqueous phases may be extracted twice with dichloromethane. The organic layers may be combined, dried over $Na_2SO_4$, and concentrated to obtain compound 2. The identity and purity of the compound 2 may be confirmed by $^1H$ and $^{13}C$ NMR spectroscopic, and HPLC analysis.

According to some embodiments of the present disclosure, in the following examples, the catalyst containing copper or iron may be Fe, $Fe_2O_3$, $FeCl_3$, $Fe(acac)_3$, Cu, CuO, CuI, $Cu(acac)_2$, or a combination thereof.

According to some embodiments of the present disclosure, in the following examples, the first base may be $Cs_2CO_3$, $K_2CO_3$, $K_3PO_4$, sodium methoxide ($CH_3ONa$), sodium ethoxide ($C_2H_5ONa$), sodium tert-butoxide, or a combination thereof.

According to some embodiments of the present disclosure, in the following examples, the first solvent may be DMF, DMSO, $CH_3CN$ or a combination thereof.

According to some embodiments of the present disclosure, in the method disclosed herein, a compound of formula 2 may be formed from the compound of formula XIV and the compound of formula 3 by means of a coupling reaction, the reaction in step (A) is performed at a temperature from 80° C. to 135° C., the step (A) reaction may be stirred and kept for a period of time, in some embodiments, the period of time is from 10 hours to 32 hours. In some embodiments, the formula 3 in step (A) may be used at an amount of 0.95 equivalent to 2.5 equivalents per 1 equivalent by mole of the formula XIV. The first base in step (A) may be used at an amount of 1.5 equivalents to 3 equivalents per 1 equivalent by mole of the formula XIV. The catalyst in step (A) may be used at an amount of 0.05 equivalent to 0.5 equivalent per 1 equivalent by mole of the formula XIV.

According to some embodiments of the present disclosure, in the method disclosed herein, the reaction in step (A) is performed at a temperature from 80° C. to 135° C. In other embodiments, the reaction temperature is from 90° C. to 120° C. In still other embodiments, the reaction temperature is 100° C.

According to some embodiments of the present disclosure, in the method disclosed herein, the step (A) reaction was stirred and kept for a period of time, in some embodiments, the period of time is from 10 hours to 32 hours. In other embodiments, the period of time is from 15 hour to 24 hours.

According to some embodiments of the present disclosure, in the method disclosed herein, in some embodiments, the formula 3 in step (A) may be used at an amount of 0.95 equivalent to 2.5 equivalents per 1 equivalent by mole of the formula XIV. In other embodiments, the amount is 1.0 equivalent to 2.0 equivalents per 1 equivalent by mole of the formula XIV. In yet other embodiments, the amount is 1.2 equivalents to 1.5 equivalents per 1 equivalent by mole of the formula XIV.

According to some embodiments of the present disclosure, in the method disclosed herein, in some embodiments, the first base in step (A) may be used at an amount of 1.5 equivalents to 3 equivalents per 1 equivalent by mole of the formula XIV. In other embodiments, the amount is 2.0 equivalents to 2.5 equivalents per 1 equivalent by mole of the formula XIV.

According to some embodiments of the present disclosure, in the method disclosed herein, in some embodiments, the catalyst in step (A) may be used at an amount of 0.05 equivalent to 0.5 equivalent per 1 equivalent by mole of the formula XIV. In other embodiments, the amount is 0.1 equivalent to 0.4 equivalent per 1 equivalent by mole of the formula XIV.

According to one embodiment of the present disclosure, in the method disclosed herein, a first reactor containing DMF may be provided, and then $Fe(acac)_3$ (212 mg, 0.6 mmol), CuO (16 mg, 0.2 mmol) and Cs$_2$CO$_3$ (1.3 g, 4.0 mmol) may be dissolved in DMF (10 mL). Subsequently, compound XIV (832 mg, 2.0 mmol), compound 3 (510 mg, 3.0 mmol) may be added to this mixture to obtain a first mixture. Then the first reactor may be sealed under nitrogen, and the first mixture may be heated and kept at 90° C., stirred for 20 hours. After cooling to room temperature, the first mixture may be diluted with dichloromethane (10 mL) and filtered to obtain a first filtrate. The first filtrate may be washed twice with water (2×10 mL) to obtain a first combined aqueous phases, and the first combined aqueous phases may be extracted twice with dichloromethane (2×10 mL). The organic layers may be combined, dried over Na$_2$SO$_4$, and concentrated to obtain compound 2 (796 mg, yield 82%).

Step (B): cyclization reaction

The compound XVII is a key intermediate for preparing CH5424802. The cyclization reaction may be taken place when compound 2 reacts with compound 4 in base environment to give compound XVII.

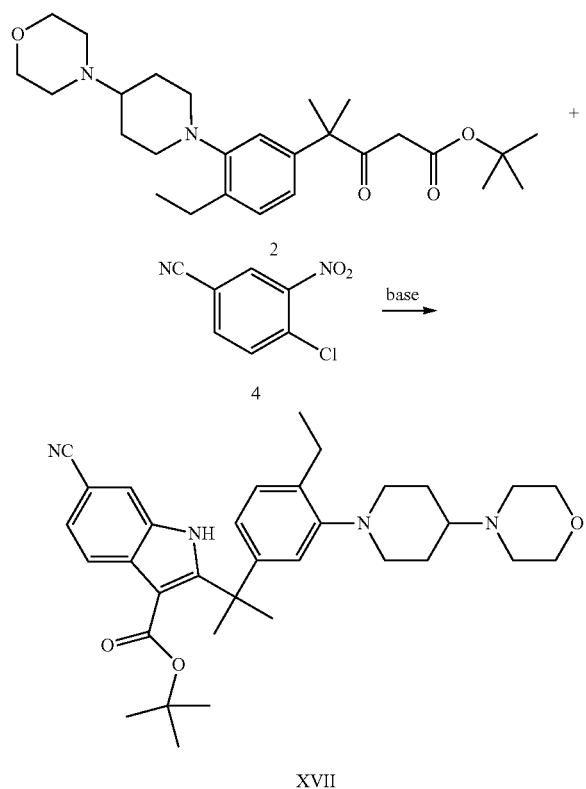

In a second reactor, compound 2, compound 4 and a second base, may be added to a second solvent (dry organic solvent). Then the second reactor may be sealed under nitrogen, and the mixture may be kept at 25° C.~40° C., stirred for 8 hours to 15 hours. After the reaction, the mixture may be diluted with dichloromethane and filtered. The filtrate may be washed twice with water, and the combined aqueous phases may be extracted twice with dichloromethane. The organic layers may be combined, dried over Na$_2$SO$_4$, and concentrated to obtain compound XVII. The identity and purity of the compound XVII may be confirmed by $^1$H and $^{13}$C NMR spectroscopic, and HPLC analysis.

According to some embodiments of the present disclosure, in the following examples, the second base may be Cs$_2$CO$_3$, K$_2$CO$_3$, K$_3$PO$_4$, or a combination thereof.

According to some embodiments of the present disclosure, in the following examples, the second solvent may be DMF, THF or a combination thereof.

According to some embodiments of the present disclosure, in the method disclosed herein, a compound of formula XVII may be formed from the compound of formula 2 and formula 4 by means of a cyclization reaction, the reaction in step (B) may be performed at a temperature from 25° C. to 40° C., the step (B) reaction may be stirred and kept for a period of time, in some embodiments, the period of time may be from 8 hours to 15 hours. In some embodiments, the formula 4 in step (B) may be used at an amount of 1.0 equivalent to 2.0 equivalents per 1 equivalent by mole of the formula 2. In some embodiments, the second base in step (B) may be used at an amount of 0.4 equivalent to 0.6 equivalent per 1 equivalent by mole of the formula 2.

According to some embodiments of the present disclosure, in the method disclosed herein, the reaction in step (B) is performed at a temperature from 25° C. to 40° C. In other embodiments, the reaction temperature is from 30° C. to 35° C.

According to some embodiments of the present disclosure, in the method disclosed herein, the step (B) reaction was stirred and kept for a period of time, in some embodiments, the period of time is from 8 hours to 15 hours. In other embodiments, the period of time is from 10 hour to 12 hours.

According to some embodiments of the present disclosure, in the method disclosed herein, in some embodiments, the formula 4 in step (B) may be used at an amount of 1.0 equivalent to 2.0 equivalents per 1 equivalent by mole of the formula 2, in some embodiments, the amount is 1.1 equivalent to 1.5 equivalents per 1 equivalent by mole of the formula 2.

According to some embodiments of the present disclosure, in the method disclosed herein, in some embodiments, the second base in step (B) may be used at an amount of 0.4 equivalent to 0.6 equivalent per 1 equivalent by mole of the formula 2. In other embodiments, the amount is 0.5 equivalent per 1 equivalent by mole of the formula 2.

According to one embodiment of the present disclosure, in the method disclosed herein, a second reactor containing dry DMF may be provided, and then compound 2 (917 mg, 2.0 mmol), compound 4 (210 mg, 2.3 mmol) and Cs$_2$CO$_3$ (325 mg, 1.0 mmol) may be added to dry DMF (10 mL) to obtain a second mixture. Then the second reactor may be sealed under nitrogen, and the second mixture may be kept at 35° C., stirred for 10 hours. After the reaction, the second mixture may be diluted with dichloromethane (10 mL) and filtered to obtain a second filtrate. The second filtrate may be washed twice with water (2×10 mL) to obtain a second combined aqueous phases, and the second combined aqueous phases may be extracted twice with dichloromethane (2×10 mL). The organic layers may be combined, dried over Na$_2$SO$_4$, and concentrated to obtain compound XVII as a light yellow powder (1013 mg, yield 91.0%), HPLC purity: 99.0%.

According to some embodiments of present disclosure, wherein, the compound XVIII and compound 1 can be obtained according to a reference literature (Drug of the future. 2013, 38(12), 799-805).

In the present invention, the term "comprise" is an open expression, it means comprising the contents disclosed herein, but don't exclude other contents.

In the prior art, the reaction for the synthesis of ALK inhibitor CH5424802 and intermediates thereof are first carried out with cyclization reaction, then with condensation reaction. There are some disadvantages, for example, use expensive, harmful heavy metal to environment pollution, need isomeric separation for industrial production, react in strictly anhydrous environment. The method of present disclosure may avoid the above mentioned disadvantages. We improve a process for the synthesis of CH5424802 and intermediates thereof, we first couple with 4-(piperidin-4-yl)morpholine fragment, then cyclize with 3-nitro-chloro-acrylonitrile. We use containing copper or iron as catalyst, which are low toxicity, cheap, easy to get, environmentally and friendly, and is economical and industrially applicable. It reduce the cost of industrial production so greatly and it is a green synthetic route.

EXAMPLES

The preparation methods of ALK inhibitor CH5424802 and intermediates thereof are disclosed in the examples of the present disclosure. Those skilled in the art can learn from this article to properly improve the process parameters to implement the preparation method. It's to note that all the similar replacements and changes are obvious for the skilled person and within the scope of the present disclosure. The methods disclosed herein are described in the preferred examples. Related persons can clearly realize and apply the techniques disclosed herein by making some changes, appropriate alterations or combinations to the methods without departing from spirit, principles and scope of the present disclosure.

In order to further understand the invention, it is detailed below through examples.

Example 1

Preparation of Compound 2

In a reactor, $Fe_2O_3$ (16 mg, 0.1 mmol), and $K_2CO_3$ (414 mg, 3.0 mmol) were dissolved in DMSO (12 mL). Subsequently, compound XIV (832 mg, 2.0 mmol) and compound 3 (323 mg, 1.9 mmol) were added to this mixture. Then the reactor was sealed under nitrogen, and the mixture was heated and kept at 80° C., stirred for 32 hours. After cooling to room temperature, the mixture was diluted with dichloromethane (12 mL) and then filtered. The resulting filtrate was washed twice with water (2×12 mL), and aqueous phases were combined, then the combined aqueous phases were extracted twice with dichloromethane (2×12 mL). The organic layers were combined, dried over $Na_2SO_4$, and concentrated to obtain compound 2 (747 mg, yield 77%).

Example 2

Preparation of Compound 2

In a reactor, $Fe(acac)_3$ (212 mg, 0.6 mmol), CuO (16 mg, 0.2 mmol), and $Cs_2CO_3$ (1.3 g, 4.0 mmol) were dissolved in DMF (10 mL). Subsequently, compound XIV (832 mg, 2.0 mmol) and compound 3 (510 mg, 3.0 mmol) were added to this mixture. Then the reactor was sealed under nitrogen, and the mixture was heated and kept at 90° C., stirred for 20 hours. After cooling to room temperature, the mixture was diluted with dichloromethane (10 mL) and then filtered. The resulting filtrate was washed twice with water (2×10 mL), and aqueous phases were combined, then the combined aqueous phases were extracted twice with dichloromethane (2×10 mL). The organic layers were combined, dried over $Na_2SO_4$, and concentrated to obtain compound 2 (796 mg, yield 82%).

Example 3

Preparation of Compound 2

In a reactor, CuI (38.1 mg, 0.2 mmol), and $K_3PO_4$ (849 mg, 4.0 mmol) were dissolved in DMF (15 mL). Subsequently, compound XIV (832 mg, 2.0 mmol) and compound 3 (850 mg, 5.0 mmol) were added to this mixture. Then the reactor was sealed under nitrogen, and the mixture was heated and kept at 135° C., stirred for 10 hours. After cooling to room temperature, the mixture was diluted with dichloromethane (15 mL) and then filtered. The resulting filtrate was washed twice with water (2×15 mL), and aqueous phases were combined, then the combined aqueous phases were extracted twice with dichloromethane (2×15 mL). The organic layers were combined, dried over $Na_2SO_4$, and concentrated to obtain compound 2 (772 mg, yield 79.5%).

Example 4

Preparation of Compound 2

In a reactor, $FeCl_3$ (64.8 mg, 0.4 mmol), and $CH_3ONa$ (216 mg, 4.0 mmol) were dissolved in $CH_3CN$ (10 mL). Subsequently, compound XIV (832 mg, 2.0 mmol) and compound 3 (340 mg, 2.0 mmol) were added to this mixture. Then the reactor was sealed under nitrogen, and the mixture was heated and kept at 100° C., stirred for 15 hours. After cooling to room temperature, the mixture was diluted with dichloromethane (10 mL) and then filtered. The resulting filtrate was washed twice with water (2×10 mL), and aqueous phases were combined, then the combined aqueous phases were extracted twice with dichloromethane (2×10 mL). The organic layers were combined, dried over $Na_2SO_4$, and concentrated to obtain compound 2 (781 mg, yield 80.5%).

Example 5

Preparation of Compound 2

In a reactor, $Fe_2O_3$ (84 mg, 0.4 mmol), $Cu(acac)_2$ (157 mg, 0.6 mmol), and $C_2H_5ONa$ (408 mg, 6.0 mmol) were dissolved in DMSO (20 mL). Subsequently, compound XIV (832 mg, 2.0 mmol) and compound 3 (408 mg, 2.4 mmol) were added to this mixture. Then the reactor was sealed under nitrogen, and the mixture was heated and kept at 85° C., stirred for 24 hours. After cooling to room temperature, the mixture was diluted with dichloromethane (20 mL) and then filtered. The resulting filtrate was washed twice with water (2×20 mL), and aqueous phases were combined, then the combined aqueous phases were extracted twice with dichloromethane (2×20 mL). The organic layers were combined, dried over $Na_2SO_4$, and concentrated to obtain compound 2 (786 mg, yield 81%).

Example 6

Preparation of Compound 2

In a reactor, CuO (32 mg, 0.4 mmol), and sodium tert-butoxide (384 mg, 4.0 mmol) were dissolved in DMF (12 mL). Subsequently, compound XIV (832 mg, 2.0 mmol) and compound 3 (680 mg, 4.0 mmol) were added to this mixture. Then the reactor was sealed under nitrogen, and the mixture was heated and kept at 120° C., stirred for 12 hours. After cooling to room temperature, the mixture was diluted with dichloromethane (12 mL) and then filtered. The resulting filtrate was washed twice with water (2×12 mL), and aqueous phases were combined, then the combined aqueous phases were extracted twice with dichloromethane (2×12 mL). The organic layers were combined, dried over $Na_2SO_4$, and concentrated to obtain compound 2 (757 mg, yield 78%).

Example 7

Preparation of Compound XVII

In a reactor, compound 2 (917 mg, 2.0 mmol), compound 4 (210 mg, 2.3 mmol) and $Cs_2CO_3$ (325 mg, 1.0 mmol) were added to dry DMF (10 mL). Then the reactor was sealed under nitrogen, and the mixture was kept at 35° C., stirred for 10 hours. After the reaction, the mixture was diluted with dichloromethane (10 mL) and then filtered. The resulting filtrate was washed twice with water (2×10 mL), and aqueous phases were combined, then the combined aqueous phases were extracted twice with dichloromethane (2×10 mL). The organic layers were combined, dried over $Na_2SO_4$, and concentrated to obtain compound XVII as a light yellow powder (1013 mg, yield 91.0%), HPLC purity: 99.0%.

Example 8

Preparation of Compound XVII

In a reactor, compound 2 (917 mg, 2.0 mmol), compound 4 (183 mg, 2.0 mmol) and $K_2CO_3$ (166 mg, 1.2 mmol) were added to dry THF (20 mL). Then the reactor was sealed under nitrogen, and the mixture was kept at 25° C., stirred for 15 hours. After the reaction, the mixture was diluted with dichloromethane (10 mL) and then filtered. The resulting filtrate was washed twice with water (2×10 mL), and the aqueous phases were combined, then combined aqueous phases were extracted twice with dichloromethane (2×10 mL). The organic layers were combined, dried over $Na_2SO_4$, and concentrated to obtain compound XVII as a light yellow powder (952 mg, yield 85.5%), HPLC purity: 99.2%.

Example 9

Preparation of Compound XVII

In a reactor, compound 2 (917 mg, 2.0 mmol), compound 4 (365 mg, 4 mmol) and $K_3PO_4$ (170 mg, 0.8 mmol) were added to dry DMF (15 mL). Then the reactor was sealed under nitrogen, and the mixture was kept at 40° C., stirred for 8 hours. After the reaction, the mixture was diluted with dichloromethane (10 mL) and then filtered. The resulting filtrate was washed twice with water (2×10 mL), and aqueous phases were combined, then the combined aqueous phases were extracted twice with dichloromethane (2×10 mL). The organic layers were combined, dried over $Na_2SO_4$, and concentrated to obtain compound XVII as a light yellow powder (968 mg, yield 87.0%), HPLC purity: 98.8%.

Example 10

Preparation of Compound XVII

In a reactor, compound 2 (917 mg, 2.0 mmol), compound 4 (274 mg, 3.0 mmol) and $Cs_2CO_3$ (325 mg, 1.0 mmol) were added to dry THF (20 mL). Then the reactor was sealed under nitrogen, and the mixture was kept at 30° C., stirred for 12 hours. After the reaction, the mixture was diluted with dichloromethane (10 mL) and then filtered. The resulting filtrate was washed twice with water (2×10 mL), and aqueous phases were combined, then the combined aqueous phases were extracted twice with dichloromethane (2×10 mL). The organic layers were combined, dried over $Na_2SO_4$, and concentrated to obtain compound XVII as a light yellow powder (1004 mg, yield 90.2%), HPLC purity: 99.2%.

In the specification, Unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing a compound of formula XVII, comprising:
 (1) contacting a compound of formula XIV with a compound of formula 3 to obtain a compound of formula 2

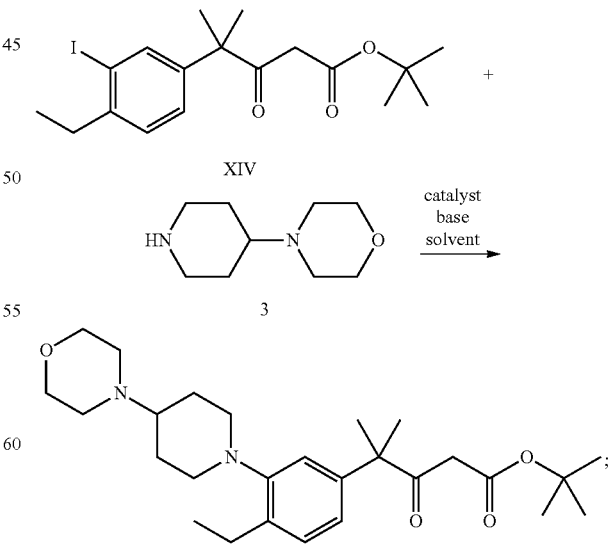

and
(2) contacting the compound of formula 2 with a compound of formula 4 to obtain a compound of formula XVII

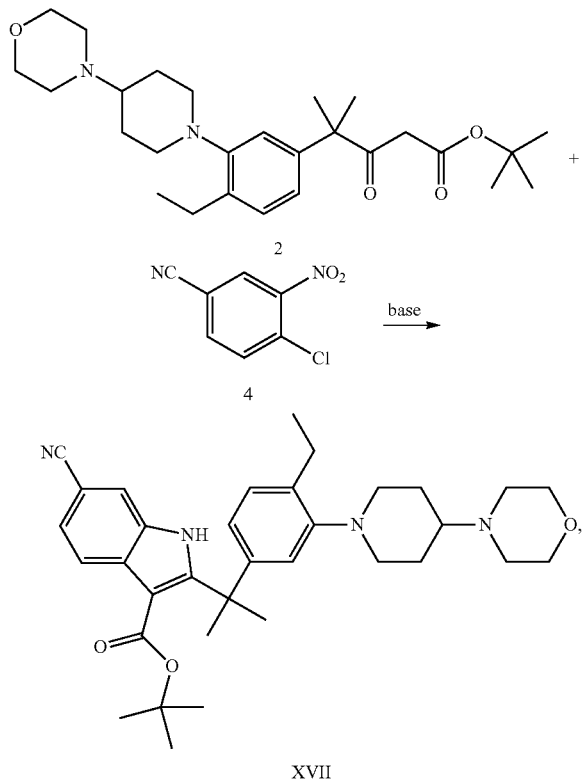

wherein in the step (1), the compound of formula XIV is contacted with the compound of formula 3 in a first solvent selected from a group consisting of DMF, DMSO and CH3CN, or a combination thereof in the presence of a catalyst and a first base, the catalyst is selected from a group consisting of Fe, $Fe_2O_3$, $FeCl_3$, $Fe(acac)_3$, Cu, CuO, CuI, and $Cu(acac)_2$, or a combination thereof, wherein the first base is selected from a group consisting of $Cs_2CO_3$, $K_2CO_3$, $K_3PO_4$, sodium methoxide ($CH_3ONa$), sodium ethoxide ($C_2H_5ONa$), and sodium tert-butoxide, and wherein in the step (2), the compound of formula 2 is contacted with the compound of formula 4 in the presence of a second base selected from a group consisting of $Cs_2CO_3$, $K_2CO_3$, $K_3PO_4$, or a combination thereof.

2. The method of claim 1, wherein the compound of formula XIV is contacted with the compound of formula 3 under a temperature ranging from 80° C. to 135° C.

3. The method of claim 2, wherein the compound of formula XIV is contacted with the compound of formula 3 with stirring for 10 hours to 32 hours.

4. The method of claim 3, wherein the amount of the compound of formula 3 is 0.95 equivalent to 2.5 equivalents per 1 equivalent by mole of the compound of formula XIV.

5. The method of claim 1, wherein the amount of the catalyst is 0.05 equivalent to 0.5 equivalent per 1 equivalent by mole of the compound of formula XIV.

6. The method of claim 1, wherein the amount of the first base is 1.5 equivalents to 3 equivalents per 1 equivalent by mole of the compound of formula XIV.

7. The method of claim 1, wherein compound of formula 2 is reacted with the compound of formula 4 under a temperature ranging from 25° C.~40° C.

8. The method of claim 1, wherein the compound of formula 2 is reacted with the compound of formula 4 with stirring for 8 hours to 15 hours.

9. The method of claim 1, wherein the compound of formula 2 is contacted with the compound of formula 4 in a second solvent selected from a group consisting of DMF and THF, or a combination thereof.

10. The method of claim 1, wherein the amount of the second base is 0.4 equivalent to 0.6 equivalent per 1 equivalent by mole of the compound of formula 2.

11. The method of claim 1, wherein the compound of formula 2 is obtained by steps of:
providing a first reactor containing DMF;
dissolving $Fe(acac)_3$ (212 mg, 0.6 mmol), CuO (16 mg, 0.2 mmol), and Cs2CO3 (1.3 g, 4.0 mmol) in DMF (10 mL), adding the compound of formula XIV (832 mg, 2.0 mmol), compound 3 (510 mg, 3.0 mmol) to obtain a first mixture,
sealing the first reactor under nitrogen, heating the first mixture, and keeping the temperature of the first mixture at 90° C. with stirring for 20 hours;
cooling the first mixture to room temperature, and diluting the first mixture by dichloromethane (10 mL) and filtering the resulting mixture to obtain a first filtrate;
washing the filtrate twice with water (2×10 mL) to obtain a first combined aqueous phases;
extracting the first combined aqueous phases twice with dichloromethane (2×10 mL), and collecting an organic layer;
drying and concentrating the organic layer to obtain the compound of formula 2 (796 mg, yield 82%).

12. The method of claim 1, wherein the compound of formula XVII is obtained by steps of:
providing a second reactor containing dry DMF (10 mL);
adding the compound of formula 2 (917 mg, 2.0 mmol), the compound of formula 4 (210 mg, 2.3 mmol) and $Cs_2CO_3$ (325 mg, 1.0 mmol) to dry DMF (10 mL) to obtain a second mixture;
sealing the second reactor under nitrogen, and keeping the temperature of the mixture at 35° C. with stirring for 10 hours;
diluting the second the mixture with dichloromethane (10 mL) and filtering the resulting mixture to obtain a second filtrate;
washing the second filtrate twice with water (2×10 mL) to obtain a second combined aqueous phases;
extracting the second combined aqueous phases twice with dichloromethane (2×10 mL), and collecting an organic layer;
drying and concentrating the organic layer to obtain the compound of formula XVII as a light yellow powder (1013 mg, yield 91.0%), HPLC purity: 99.0%.

13. The method of claim 7, wherein the amount of the compound of formula 4 is 1.0 equivalent to 2.0 equivalents per 1 equivalent by mole of the compound of formula 2.

* * * * *